United States Patent
Seth et al.

[11] Patent Number: 5,824,341
[45] Date of Patent: Oct. 20, 1998

[54] COMPOSITION PROVIDING SELECTIVE RELEASE OF AN ACTIVE INGREDIENT

[75] Inventors: Pawan Seth, Strasbourg; Andre Stamm, Griesheim, both of France

[73] Assignee: Pharma Pass, France

[21] Appl. No.: 776,797

[22] PCT Filed: Aug. 11, 1995

[86] PCT No.: PCT/FR95/01079

§ 371 Date: Apr. 22, 1997

§ 102(e) Date: Apr. 22, 1997

[87] PCT Pub. No.: WO96/04893

PCT Pub. Date: Feb. 22, 1996

[30] Foreign Application Priority Data

Aug. 11, 1994 [FR] France ................... 94 09963

[51] Int. Cl.$^6$ ....................................... A61K 9/22
[52] U.S. Cl. .................. 424/473; 424/489; 424/472
[58] Field of Search .................... 424/489, 473, 424/472, 449

[56] References Cited

U.S. PATENT DOCUMENTS

| | | | |
|---|---|---|---|
| 4,968,208 | 11/1990 | Oren et al. | 424/468 |
| 5,178,868 | 1/1993 | Malmqvist-Granlund et al. | 424/490 |
| 5,229,131 | 7/1993 | Amidon | 424/451 |
| 5,358,502 | 10/1994 | Herbig | 604/892.1 |
| 5,445,828 | 8/1995 | Pozzi | 424/476 |
| 5,536,507 | 7/1996 | Abramowitz | 424/479 |
| 5,558,879 | 9/1996 | Chen et al. | 424/480 |
| 5,651,985 | 7/1997 | Penners | 424/469 |
| 5,656,296 | 8/1997 | Khan et al. | 424/473 |
| 5,736,159 | 4/1998 | Chen et al. | 424/480 |

*Primary Examiner*—Thurman K. Page
*Assistant Examiner*—Kathryne E. Shelborne
*Attorney, Agent, or Firm*—Sheridan Ross PC

[57] ABSTRACT

A composition that ensures selective release of an active ingredient at a given site, and in particular, a pharmaceutical composition enabling selective release of an active ingredient to be obtained at a target organ. The composition is intended for oral administration, providing selective release of its active ingredient in the colon.

22 Claims, 1 Drawing Sheet a. core b. elastic membrane c. active ingredient d. water permeable material

COMPOSITION PROVIDING SELECTIVE RELEASE OF AN ACTIVE INGREDIENT

This application is a 371 of PCT/FR95/01079 filed Aug. 11, 1995.

FIELD OF THE INVENTION

The present invention provides a composition that ensures selective release of an active ingredient at a given site, and in particular a pharmaceutical composition enabling selective release of an active ingredient to be obtained at a target organ. The present invention more particularly relates to a pharmaceutical composition intended for oral administration, providing selective release of its active ingredient in the colon.

BACKGROUND OF THE INVENTION

Numerous pharmaceutical compositions have been developed with an aim to providing controlled release of the active ingredient. The majority of these compositions are based on the principle of delayed release or sustained release of the medicament at, or not at, a target organ.

EP-A-0,250,374 discloses coated mini-dosing units. Their core is obtained by compressing a mixture of the active ingredient with polymers that swell in water by osmosis action, the polymeric coating that surrounds the core controlling release of the medicament.

EP-A-0,077,956 discloses enteric micro-capsules containing an active compound as a core material, surrounded by a coating essentially consisting of ethyl cellulose and an enteric polymer material, a water-swellable polymer material being optionally incorporated into the core.

GB-A-2,202,143 discloses a pharmaceutical composition comprising a water-insoluble drug dispersed in a matrix consisting of microcrystalline cellulose and at least one cellulose derivative. Such a composition leads to sustained release of the active compound over a period of at least 8 hours. These compositions can be coated with an enteric coating so as to ensure release of the medicament in the intestinal tract rather than in the stomach.

The dosing units described in these documents do not make it possible to obtain immediate release of the active ingredient at a precise organ; speed of release is limited by the speed of diffusion through the matrix surrounding or trapping it, the result of this possibly being that all the administered dose is not released at the target organ. Effectively, considering the gastro-intestinal tract, transit time varies from one individual to another over a wide range, and the conditions prevailing in the gastro-intestinal system, notably as regards pH, also vary over wide degrees.

Research carried out with a view to obtaining a composition providing selective release of active ingredients at a target organ (for example the colon) were up until now centered around either the use of tablets for oral administration, coated with polymers that become decomposed by the bacteria present in the colon, or the use of tablets for oral administration, that were coated with an enteric coating.

In the first type of approach, the pro-drug concept is used, in other words a precursor of the active ingredient, the active ingredient being bound to, for example, a glucoside type polymer (Friend, Phillips et Torzen, F. Controlled Rel., 15, 47–54, (1991)). The main problem with this approach is that the medicament itself is chemically modified, and release of the active ingredient is conditioned by in-situ bacterial hydrolysis.

In the second type of approach, coatings are used consisting of polymers the solubility of which depends on pH, and which dissolve at a pH above that of the stomach. The products are unable to dissolve until the pH value of the ambient medium is above a certain value.

The use of tablets having this type of coating does not lead to satisfactory results and does not make it possible to obtain targeted release of active ingredients. In effect, if the pH profile of the gastro-intestinal tract is studied, it is noted that the pH in the distal part of the intestine varies between 6.8 and 7.2, and then falls to a value of 4.5 to 6 in the ascending colon. Consequently, the pharmaceutical composition is designed whereby the polymer coating dissolves at a pH which is greater than or equal to 7; the polymer dissolves in the intestine and the active ingredient is released at this level. However, pH varies to a large degree from one individual to another. Thus, if the pH stays at fairly low levels, the enteric coating will remain intact and the active ingredient will not be released.

It thus clearly appears that controlled release of active ingredient that is based solely on the use of a coating that selectively breaks down at a target organ, or before reaching it, does not ensure targeted release of the medicament at that organ.

WO-A-92 17165 discloses compositions containing a core, a layer of adjuvants comprising a water-soluble material and a water-insoluble material, and an enteric coating. The core contains the active ingredient in association with a swelling agent.

EP-A-0 210 540 discloses compositions comprising an inert core, a layer containing the active ingredient, a layer made of a swelling agent and an enteric coating, or an inert core, a layer containing the active ingredient with a swelling agent and an enteric coating.

These two cited documents do not allow a selective release of the active ingredient at a target organ, and furthermore involves contamination of the active ingredient with the swelling agent.

There is thus a need for a composition providing selective release of an active ingredient at a given site, and in particular for a pharmaceutical composition providing selective release of an active ingredient at a target organ.

SUMMARY OF THE INVENTION

The present invention sets out to overcome the disadvantages of existing pharmaceutical compositions, in other words non-selective and prolonged release, and of providing a composition ensuring selective release of an active ingredient at a given site, and notably a pharmaceutical composition providing selective release of the active ingredient at a target organ, in particular the colon.

The present invention consequently provides a composition comprising, successively:

(a) a core (1) consisting of a water-swellable material;

(b) a layer (2) of an elastic material that allows water to pass and is insoluble in water;

(c) a layer (3) containing at least one active ingredient; and (d) a layer (4) of a material that becomes water-permeable in a predetermined aqueous medium, this layer being able to rupture under the effect of expansion of the core (1).

This composition makes it possible to obtain a pharmaceutical composition, in particular designed for oral administration, that ensures selective release of an active ingredient at a target organ.

In the presence of the appropriate aqueous ambient medium, the material of the layer (4) is, or becomes, water-permeable; water penetrates into the composition and reaches the core (1). The core (1) swells at a speed controlled by the elastic material (2) thus exercising a certain pressure on the outer layer. After a certain time, this pressure leads to rupture of layer (4) allowing the active ingredient (3) layer to come in contact with the surrounding medium, which leads to immediate release of all the active ingredient. Thanks to the layer (2) which allows water to pass through but which is substantially water-insoluble, the active ingredient is not able to migrate into the core. In-situ formation of a sustained-release or delayed dosage form is thus avoided; the disadvantages of the prior art are thus avoided.

In one preferred embodiment, in the present composition the core (1) exhibits a volume expansion of 50 to 700% preferably 100 to 500%, more preferably from 150 to 300%.

According to a further preferred feature, in the composition, the relative proportions by weight, based on the total weight of the composition, of the various constitutive elements (1) to (4) thereof are as follows:

30 to 90%, preferably 50 to 70%, more preferably about 60% by weight of (1);

1 to 6%, preferably 2 to 4%, more preferably about 3% by weight of (2);

1 to 60%, preferably 10 to 50%, more preferably about 30% by weight of (3);

3 to 15%, preferably 5 to 9%, more preferably about 7% by weight of (4).

According to a further preferred feature, in the present composition, said material of layer (4) which becomes water-permeable in a predetermined aqueous medium is a water-soluble polymeric material, the solubility of which depends on pH, said material having a solubility starting from a pH value comprised between pH=6.0 and pH=8.0.

According to an alternative embodiment of this feature, said polymeric material of layer (4) comprises a polymer material exhibiting a solubility starting from a pH value of 6.8.

According to a further preferred feature, in the present composition, the material of layer (4) is a gastro-resistant and entero-soluble material.

According to a further preferred feature, in the present composition, the active ingredient is prednisolon or a pharmaceutically-acceptable derivative thereof.

According to a further preferred feature, in the present composition, layer (3) comprises 1 to 500 mg of active ingredient and, preferably, from 5 to 100 mg of active ingredient.

The invention also relates to this composition for its use as a medicament.

According to a further preferred feature, the use as a medicament is use as a medicament for treating diseases of the colon.

The invention also provides a method for preparing a composition according to the invention, comprising the following steps:

(i) providing a compressed core (1) starting from a mixture in powder form;

(ii) coating said core (1) with a layer (2);

(iii) coating said layer (2) with a layer (3) comprising at least one active ingredient; and (iv) coating a layer (4) over said layer (3)

Any known method in the appropriate art can be used for the compression, coating, capsule preparation, tablet preparation, etc. steps. The ingredients of the layers are provided in a conventional fashion, for example in powder form, dissolved in a suitable solvent, etc.

The composition according to the invention is provided in a conventional form, for example a capsule, gelatin capsule, tablet, etc. This composition is particularly suitable for oral administration. The dose of active ingredient to be administered can be formulated either in the form of a single tablet, capsule or gelatin capsule, or in the form of mini-dosage units able to be administered in a single or several doses, as a function of the active ingredient. Such mini-units are advantageous for the implementation of this invention.

BRIEF DESCRIPTION OF THE DRAWINGS

The invention will now be described in detail with reference to FIGS. 1 and 2.

DETAILED DESCRIPTION OF THE INVENTION

Figure 1:
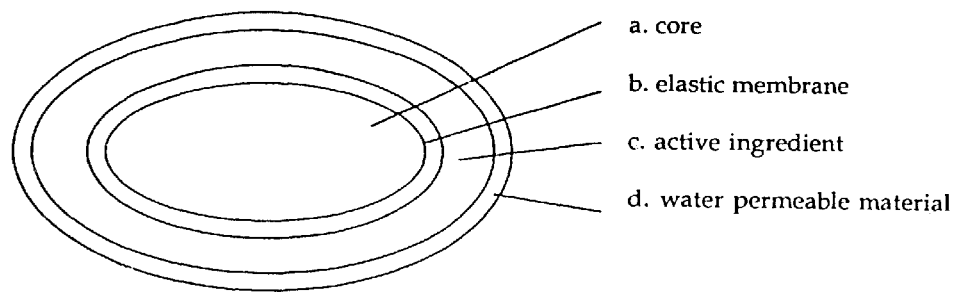
FIG. 1 is a sectional view of a composition according to the invention.

With reference now to FIG. 1, the core and the layers are respectively indicated by the references (1) to (4).

The core (1) comprises a material that swells in the presence of water, but which is non-water soluble and preferably is a neutral polymeric material.

Any known bio-compatible and/or bio-degradable polymeric material conventionally employed can be incorporated into the composition according to the present invention. Examples of these are: methyl celluloses having varying molecular weights, polyvinyl alcohols, acrylic polymers, hydroxypropylmethyl celluloses, and, generally speaking, any natural or synthetic polymer together with copolymers derived therefrom and mixtures derived from them able to swell in contact with water or an aqueous fluid.

The core can optionally include any conventionally used excipient in this field.

Layer (2) which is placed over the core constitutes a barrier preventing the active ingredient from migrating into the core and which controls the rate of expansion of the core. This layer consists of a material, preferably polymeric, which allows water present in the medium to reach the core, which is elastic and substantially non-water soluble. This material can, for example, be porous. One can use all materials, polymers, copolymers and mixtures deriving therefrom having the characteristics defined above. Polymer (2) has an elasticity which is defined as follows: the capacity to at least double in volume in contact with water at 37° C., without rupture of the peripheral film. Examples of such compounds are: ethyl cellulose plus hydroxypropylmethyl cellulose, methyl cellulose plus hydroxypropylmethyl cellulose, Eudragit® NE30D, etc.

It has also been determined that a composition comprising at least one hydrophilic polymer material and a plastifying agent leads to a layer having significant elasticity.

Layer (3) comprises at least one active ingredient either alone or mixed with excipients used conventionally in the pharmaceutical field, or any other field, as a function of the final use of the active ingredient. The active ingredient may be a biocide, an acaricide, an insecticide, a bactericide, a fungicide, a medicament, etc., and is preferably a compound having pharmaceutical activity. Any water-soluble or insoluble compound having activity can be employed.

Layer (3) can also be composed of sub-layers, for example containing different active ingredients, optionally separated by sub-layers in appropriate materials.

Below, and for the sake of ease and simplicity, reference will be made to a pharmaceutical composition obtained from an active ingredient that is pharmaceutically active.

Layer (4) consists of a material that becomes water-permeable, and which is able to rupture under the effect of expansion of the core. The expression "material becoming water-permeable in a predetermined aqueous medium" means that the material allows water to pass, or is able to allow water to pass after exposure to this given medium. The expression "aqueous medium" is used here in the conventional meaning of the term. For example, the material may become porous under the effect of its solubility in the medium or as a result of its breakdown under the conditions prevailing in said medium. The material is able to rupture under the effect of the expansion of the core (1), once the water, after having passed through the layer (4), (3) and (2) has caused the core (1) to swell.

This layer (4) can consist of a material, preferably polymeric, able to be broken down or dissolved by an element present specifically upstream of a site, or at the given site where release should take place. For example, this material may correspond to an enteric polymer that breaks down or dissolves under the effect of a given pH, or may correspond to a polymer which is specifically broken down by a given enzyme, for example a pancreatic or intestinal enzyme such as an esterase.

Any coating, preferably enteric, employed conventionally in the pharmaceutical field can be used in the framework of this invention. Examples of suitable compounds are: acrylic polymers such as Eudragit® in combination with a plastifying agent such as dibutyl phtalate, triethyl citrate, etc.

The core (1) and the layer (2) to (4) may optionally contain appropriate additives known in the art, such as, for example, stabilizers, anti-oxidants, coloring agents, plastifiers, lubricants, preservatives, flavoring agents, compression agents, etc. Moreover, additional layers may be provided such as, for example, an outer layer which confers a flavor and/or a color and/or which improves the acceptability of the medicament and/or allows marking.

As indicated above, the mechanism is as follows: in the presence of the surrounding appropriate aqueous medium, the material of layer (4) allows water to pass through. The core (1), in the presence of water, swells at a speed that is controlled by the polymeric coating (2), exercising a certain pressure on the outer layer. After a certain time, this pressure leads to the layer (4) rupturing, bringing the active ingredient layer (3) into contact with the surrounding medium, leading to immediate release of all the active ingredient. Thanks to the layer (2) which allows water to pass through but which is substantially insoluble in water, the active ingredient is unable to migrate into the core.

The present composition provides, by double control, in other words control of the expansion of core (1) provided by elastic layer (2) and control of the place of breakdown of layer (4), selective and immediate release of the active ingredient (3) to be obtained at a given site, such as for example, and preferably, a target organ when the composition is, preferably, a pharmaceutical composition.

The composition of the layers (1), (2), (3) and (4) will be modified as a function of the required rate of expansion of core (1). It can be notably noticed that the more the materials, preferably polymeric, (2) and (4) are hydrophilic, the greater is the rate of penetration of water and the quicker the core will swell. Moreover, the rate of release of the active ingredient can be controlled by the nature of the constituents of the core, providing more or less pronounced expansion.

If it is for example desired for the pharmaceutical composition to release the active ingredient at colon level, then layer (4) can consist of an enteric coating (in other words gastro-resistant and entero-soluble) the solubility of which depends on pH. In such a case, when the pharmaceutical system finds itself in the presence of a surrounding medium the pH of which is above or equal to the value for which the (polymeric) material (4) dissolves, the layer (4) will start to dissolve leading to the formation of pores allowing gastrointestinal fluid to penetrate into the composition. Gastrointestinal fluid penetration will cause the core to swell and the rate of expansion in the core now needs to be controlled so that the coating (4) only ruptures at colon level.

The following examples illustrate the invention without however limiting its scope.

EXAMPLE 1

Using conventional methods, a tablet is prepared having the following characteristics:

Composition of Core (1):
  hydroxypropyl methyl cellulose: 26.00 mg
  microcrystalline cellulose: 52.00 mg
  hydroxypropyl cellulose: 35.00 mg (low degree of substitution. L-HPC®)
  colloidal silica: 1.50 mg
  magnesium stearate: 0.50 mg Composition of Layer (2):
  ethyl cellulose: 3.00 mg
  hydroxypropyl methyl cellulose: 2.50 mg
  dibutyl phtalate: 1.50 mg Composition of Layer (3):
  prednisolon metasulfobenzoate: 31.43 mg
  hydroxypropyl methyl cellulose: 20.00 mg Composition of Layer (4):
  Eudragit® S100: 14.00 mg
  dibutyl phtalate: 3.50 mg

EXAMPLE 2

Using conventional methods, a tablet is prepared having the following characteristics:

Composition of Core (1):
  hydroxypropyl methyl cellulose: 26.00 mg
  microcrystalline cellulose: 52.00 mg
  hydroxypropyl cellulose: 35.00 mg (low degree of substitution. L-HPC®)
  colloidal silica: 1.50 mg
  magnesium stearate: 0.50 mg Composition of Layer (2):
  ethyl cellulose: 3.00 mg
  hydroxypropyl methyl cellulose: 2.50 mg
  triethyl citrate: 1.50 mg Composition of Layer (3):
  prednisolon metasulfobenzoate: 31.43 mg
  hydroxypropyl methyl cellulose: 20.00 mg Composition of Layer (4):
  Eudragit® S100: 10.00 mg
  hydroxypropyl methyl cellulose: 4.00 mg
  triethyl citrate: 3.50 mg

EXAMPLE 3

Using conventional methods, a tablet is prepared having the following characteristics:

Composition of Core (1):
- hydroxypropyl methyl cellulose: 26.00 mg
- microcrystalline cellulose: 52.00 mg
- hydroxypropyl cellulose: 35.00 mg (low degree of substitution. L-HPC®)
- colloidal silica: 1.50 mg
- magnesium stearate: 0.50 mg Composition of Layer (2):
- Eudragit® NE30D: 5.00 mg Composition of Layer (3):
- prednisolon metasulfobenzoate: 31.43 mg
- hydroxypropyl methyl cellulose: 20.00 mg Composition of Layer (4):
- Eudragit® S100: 10.00 mg
- hydroxypropyl methyl cellulose: 4.00 mg
- triethyl citrate: 3.50 mg

EXAMPLE 4

Using conventional methods, a tablet is prepared having the following characteristics:

Composition of Core (1):
- hydroxypropyl methyl cellulose: 26.00 mg
- microcrystalline cellulose: 52.00 mg
- hydroxypropyl cellulose: 35.00 mg (low degree of substitution. L-HPC®)
- colloidal silica: 1.50 mg
- magnesium stearate: 0.50 mg Composition of Layer (2):
- Eudragit® NE30D: 5.00 mg Composition of Layer (3):
- prednisolon metasulfobenzoate: 31.43 mg
- hydroxypropyl methyl cellulose: 20.00 mg Composition of Layer (4):
- hydroxypropyl methyl cellulose: 15.00 mg
- dibutyl phtalate: 3.50 mg

EXAMPLE 5

An in-vivo investigation of the medicament was carried out on six healthy volunteers (3 males, 3 females). Placebo tablets were prepared containing 2 mg Sm 153 isotope enriched samarium oxide, starting from the composition of example 1 in which the active ingredient was replaced by a cellulose derivative. These tablets were administered to the patients. Using conventional scintigraphic techniques, the anatomical position and disintegration time of the tablet were determined.

Figure 2:
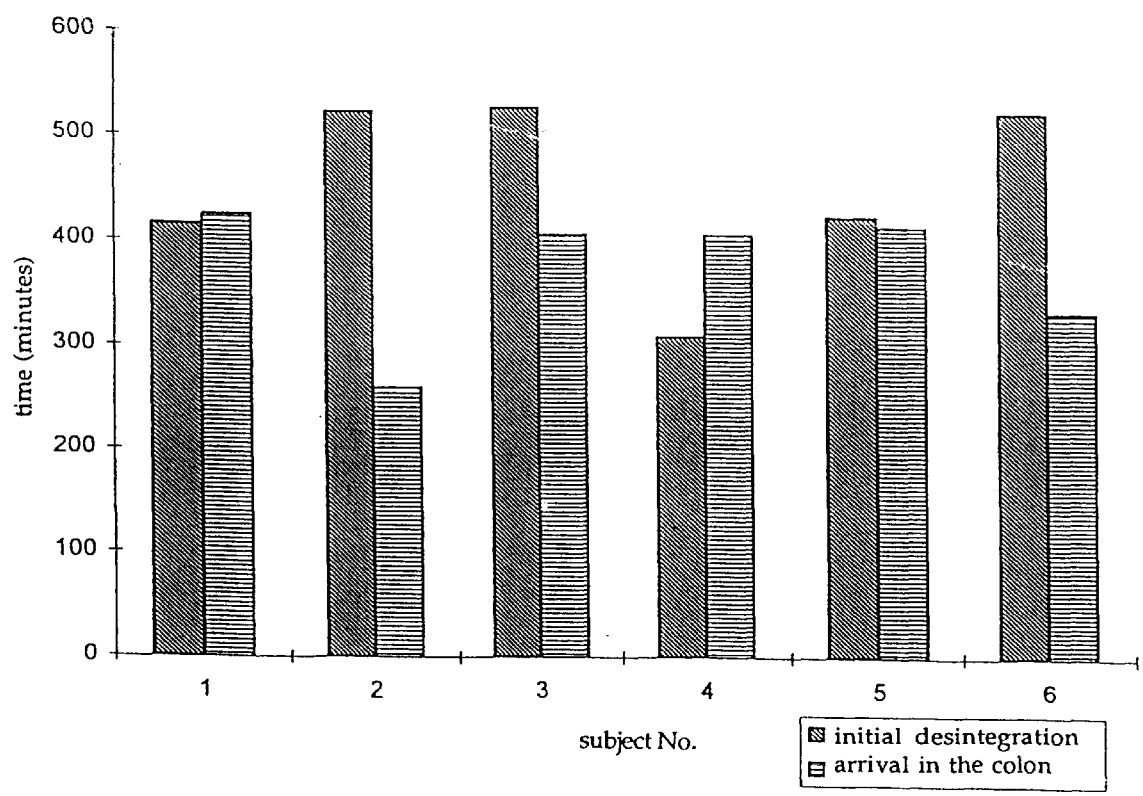
FIG. 2 is a graph showing the release profile for a composition according to the invention.

After a light breakfast, each subject received a tablet with 200 ml of water. The results were periodically recorded. Each subject then received a light lunch and recording continued. The results are given in FIG. 2. This figure indicating the times of arrival in the colon and the time at which initial disintegration of the tablet occurred, clearly shows that the radio-tagged placebo disintegrates at colon level, meaning that an active ingredient would be selectively and immediately also released at colon level.

What is claimed is:

1. A composition comprising, successively:
   (a) a core (1) consisting of a water-swellable material;
   (b) a layer (2) of an elastic material that allows water to pass and is insoluble in water;
   (c) a layer (3) containing at least one active ingredient; and
   (d) a layer (4) of a material that is water-permeable in a predetermined aqueous medium, wherein said layer (4) is capable of rupturing under the effect of expansion of said core (1).

2. The composition of claim 1, wherein said core (1) is capable of exhibiting a volume expansion of from about 50 to about 700%.

3. The composition of claim 1, wherein said core (1) is capable of exhibiting a volume expansion of from about 100 to about 500%.

4. The composition of claim 1, wherein said core (1) weighs from about 30 to about 90% of the total weight of said composition, said elastic material of layer (2) weighs from about 1 to about 6% of the total weight of said composition, said layer (3) containing at least one active ingredient weights from about 1 to about 60% of the total weight of said composition, and said material of layer (4) weighs from about 3 to about 15% of the total weight of said composition.

5. The composition of claim 1, wherein said core (1) weighs from about 50 to about 70% of the total weight of said composition, said elastic material of layer (2) weighs from about 2 to about 4% of the total weight of said composition, said layer (3) containing at least one active ingredient weighs from about 10 to about 50% of the total weight of said composition, and said material of layer (4) weighs from about 5 to about 9% of the total weight of said composition.

6. The composition of claim 1, wherein said material of layer (4) comprises a polymeric material that is soluble in said predetermined aqueous medium, wherein said predetermined aqueous medium has a pH of from about 6 to about 8.

7. The composition of claim 1, wherein said material of layer (4) comprises a polymer material that is soluble in said predetermined aqueous medium, wherein said predetermined aqueous medium has a pH of from about 6.8 to about 8.

8. The composition of claim 1, wherein said material of layer (4) is a gastro-resistant and entero-soluble material.

9. The composition of claim 1, wherein said layer (3) comprises from about 5 to about 100 mg of active ingredient.

10. A composition comprising, successively:
   (a) a core (1) consisting of a water-swellable material;
   (b) a layer (2) of an elastic material that allows water to pass and is insoluble in water;
   (c) a layer (3) comprising prednisolone or a pharmaceutically-acceptable derivative thereof; and
   (d) a layer (4) of a material that is water-permeable in a predetermined aqueous medium, wherein said layer (4) is capable of rupturing under the effect of expansion of said core (1).

11. The composition of claim 10, wherein said core (1) is capable of exhibiting a volume expansion of from about 50 to about 700%.

12. The composition of claim 10, wherein said core (1) is capable of exhibiting a volume expansion of from about 100 to about 500%.

13. The composition of claim 10, wherein said core (1) weighs from about 30 to about 90% of the total weight of said composition, said elastic material of layer (2) weighs from about 1 to about 6% of the total weight of said composition, said layer (3) comprising prednisolone or a pharmaceutically-acceptable derivative thereof weighs from about 1 to about 60% of the total weight of said composition, and said material of layer (4) weighs from about 3 to about 15% of the total weight of said composition.

14. The composition of claim 10, wherein said core (1) weighs from about 50 to about 70% of the total weight of said composition, said elastic material of layer (2) weighs from about 2 to about 4% of the total weight of said composition, said layer (3) comprising prednisolone or a pharmaceutically-acceptable derivative thereof weighs from about 10 to about 50% of the total weight of said composition, and said material of layer (4) weighs from about 5 to about 9% of the total weight of said composition.

15. The composition of claim 10, wherein said material of layer (4) comprises a polymeric material that is soluble in said predetermined aqueous medium, wherein said predetermined aqueous medium has a pH of from about 6 to about 8.

16. The composition of claim 10, wherein said material of layer (4) comprises a polymer material that is soluble in said predetermined aqueous medium, wherein said predetermined aqueous medium has a pH of from about 6.8 to about 8.

17. The composition of claim 10, wherein said material of layer (4) is a gastro-resistant and entero-soluble material.

18. The composition of claim 10, wherein said layer (3) comprises from about 5 to about 100 mg of prednisolone or a pharmaceutically-acceptable derivative thereof.

19. A composition comprising, successively:
   (a) a core (1) consisting of a water-swellable material, said core weighing from about 30 to about 90% of the total weight of said composition, and said core is capable of exhibiting a volume expansion of from about 100 to about 500%;
   (b) a layer (2) of a water permeable elastic material that is insoluble in water, said layer (2) weighing from about 1 to about 6% of the total weight of said composition;
   (c) a layer (3) comprising prednisolone or a pharmaceutically-acceptable derivative thereof, said layer (3) weighing from about 1 to about 60% of the total weight of said composition; and
   (d) a layer (4) of a material that is water-permeable in a predetermined aqueous medium, said layer (4) weighing from about 3 to about 15% of the total weight of said composition, wherein said layer (4) is capable of rupturing under the effect of expansion of said core (1), and wherein said material of layer (4) is soluble in said predetermined aqueous medium, wherein said predetermined aqueous medium has a pH of from about 6 to about 8.

20. A method for treating diseases of the colon comprising the step of administering a composition according to claim 1.

21. A method for treating diseases of the colon comprising the step of administering a composition according to claim 19.

22. A method for treating diseases of the colon comprising the step of administering a composition according to claim 19.

* * * * *